United States Patent [19]

Ginsburg et al.

[11] Patent Number: 5,552,842
[45] Date of Patent: Sep. 3, 1996

[54] PROCESS AND APPARATUS FOR GENERATING COMPARISON IMAGE REPRESENTATIVE OF ACTUAL SUBJECT VIEW

[75] Inventors: Arthur P. Ginsburg, Danville, Calif.; Lawrence P. Tessler, Lake Orion, Mich.; Craig Fries, Oakland; Jonathan Tifft, Berkeley, both of Calif.

[73] Assignee: Vision Sciences Research Corp., San Ramon, Calif.

[21] Appl. No.: 337,624

[22] Filed: Nov. 10, 1994

[51] Int. Cl.$^6$ ..................................................... A61B 3/10
[52] U.S. Cl. ........................... 351/205; 351/237; 351/239; 351/246
[58] Field of Search ..................................... 351/246, 205, 351/211, 221, 243, 239, 237

[56] References Cited

U.S. PATENT DOCUMENTS 4,365,873  12/1982  Ginsburg ................................. 351/239

Primary Examiner—William L. Sikes
Assistant Examiner—Hung Xuan Dang
Attorney, Agent, or Firm—Townsend and Townsend and Crew

[57] ABSTRACT

A segmented objective vision test is administered to a patient for determining a quantitative measurement of vision capability in the tested segments. Human vision can be tested in separate segments of the total vision spectrum including contrast sensitivity, or color sensitivity testing. Thereafter, an emmetropic real world image is filtered into corresponding emmetropic image segments. These corresponding emmetropic image segments are degraded into degraded image segments in correspondence with the separate test results for each corresponding separate segment of the total vision spectrum. The degraded image segments are then added to produce an objectively altered real world image. This objectively altered real world image can then be compared to the real world image of the emmetrope and a record preserved of the patient's actual vision condition as evidenced by the objective vision test and the subsequent image processing.

13 Claims, 4 Drawing Sheets

PROCESS AND APPARATUS FOR GENERATING COMPARISON IMAGE REPRESENTATIVE OF ACTUAL SUBJECT VIEW

This disclosure relates to presenting an evaluation of and record of vision testing of an individual. More specifically, a method of construction of the actual view of a patient having normal, above normal or vision defects is disclosed.

BACKGROUND OF THE INVENTION

Vision acuity tests are known. The most common is the Snellen test—the traditional array of letters, decreasing in size on subsequently read rows. Vision is rated as a result of the smallest line that the individual is able to read.

More recently, sine-wave contrast sensitivity tests have been developed. In such tests, human spatial frequency definition is broken into discrete bandwidths, typically in a chart format. For an example of such a test, see Ginsburg U.S. Pat. No. 4,365,873 issued Dec. 28, 1982 entitled Spatial Frequency and Contrast Sensitivity Test Chart for an example of a chart that utilizes such testing. The patient is subjectively tested in those discrete bandwidths. Thereafter, the sensitivity in the bandwidths is reported, In analysis of various "targets"—typically for military purposes—it has been known to hypothetically degrade views of the targets with high, medium and low contrast sensitivity levels. Thereafter, the degraded views of the targets are provided indicating how vision changes with perception of specific high, medium and low contrast sensitivity or general age groups. The presentations have not been correlated with the testing of specific individuals. Further, the resulting views have not been used as evaluation or records of objective vision tests of a specific patient.

SUMMARY OF THE INVENTION

A segmented objective vision test is administered to a patient for determining a quantitative measurement of vision function or capability in tested segments. Vision is tested in separate segments including acuity, contrast sensitivity, or color sensitivity testing. Thereafter, a real world image is filtered into corresponding image segments, the image utilized being usually—but not always—a clear, sharp. These corresponding image segments are changed (degraded or enhanced) into changed image segments in correspondence with the separate test results for each corresponding separate segment of the total vision spectrum of this vision test. The image segments are then combined to produce an objectively altered image. This objectively altered image can then be compared to the image of an emmetrope (or any other person's image) by display or image processed or a record preserved of the patient's actual vision condition as evidenced by the objective vision test and the subsequent image processing.

It will be understood that the techniques here illustrated are not necessarily confined to human observations. For example, the techniques presented here can be used to test and describe the performance of imaging systems.

In a preferred embodiment, the vision testing and image degradation occur in a frequency domain (space domains or other transform domains are possible). Vision testing in spatial contrast is divided into approximately two octave bands having a median band width of 1.5, 3, 6, 12, and 18 cycle per degree. Vision testing with separate vision segment results occurs for each vision segment. Image processing of a real world image includes first performing a Fourier transform and generating a frequency image segment for each corresponding band. Thereafter, an inverse Fourier transform is generated from each frequency image segment to produce a corresponding partial real image segment for each frequency band. During either the transform, the inverse transform, or before the addition of the image segments to produce a composite degraded image, degradation of the image segments occurs corresponding to objective vision test results. Finally, addition of the degraded images produces an image emulating the patient's actual vision for comparison to the original image of the real world scene.

Other techniques of image filtering can be used. For example, image convolution can be utilized. Specifically, filter functions can be applied to an original image—these functions having size or frequency sensitivity. Testing of an individual's sensitivity in the specific frequencies can occur. Thereafter, the original image can be convolved with filters whose orientation, size, shape and amplitudes are determined by the results of the vision test creating filtered images. Once the segments are added, a modified image will result.

It will be understood that the particular testing protocol utilized can be varied. Vision test targets with periodic frequencies can be utilized. Alternately, tests can be constructed utilizing the filter functions themselves. For example, various Gaussian shapes can be used as vision test targets of amplitude and varied image convolution. The results from recognition of such shapes in the form of recognizable fields can then be applied to the convolution and reconstruction of the perceived image of the individual.

The reader will understand that the disclosed process can be repeated for various kinds of vision sensitivity. For example, and in addition to contrast sensitivity, vision segments of color (red, green, and blue) can be used against the results of vision color testing (i.e. so-called tests for "color blindness") or visual acuity can be used against the results of visual acuity testing.

An advantage of the disclosed image processing is that a physician or motor vehicle testers can be given a record—for his own files and for display to others—which documents the vision condition of a patient at the time of the examination. This record can be used to verify and document the need for or the lack of need for prescription and treatments.

A further advantage of the disclosed image processing is that by the comparison technique disclosed, even the patient (with the impaired vision) can understand the relative degree of degradation of his or her vision compared to the norm. Assuming that the patient has significant vision degradation, they will naturally view the original real world view with that degradation—the state to which the patient presumably has grown accustomed. However, the comparison of the degraded view generated by testing and the disclosed process to the real world image will be contrasted. Specifically, the degraded view when compared to the emmetropic view demonstrates even to the visually impaired the degree of relative vision degradation.

BRIEF DESCRIPTION OF THE DRAWINGS

Other objects, features and advantages of this invention will become more apparent after referring to the following specification and attached drawings in which.

DESCRIPTION OF THE PREFERRED EMBODIMENT

Figure 1:
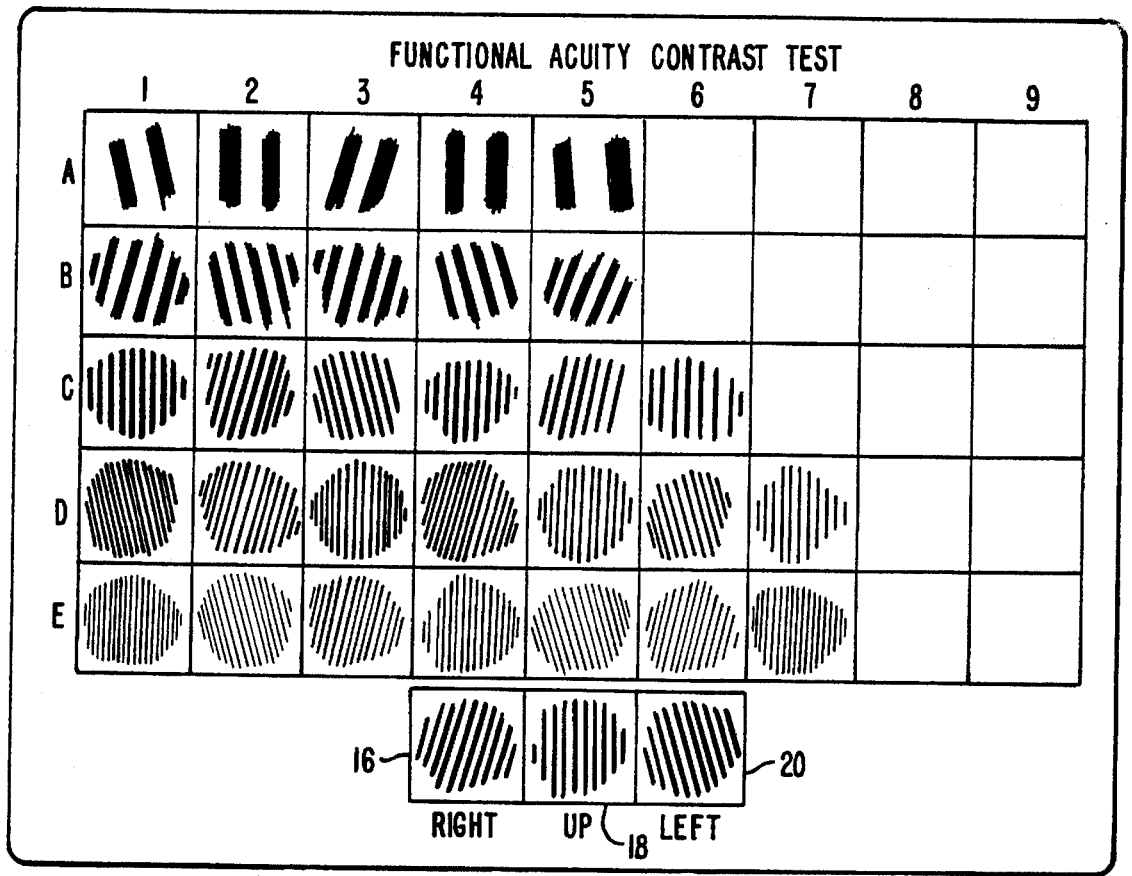
FIG. 1 is a view of a contrast sensitivity eye chart with measurement of frequency contrast sensitivity occurring in 1.5, 3, 6, 12, and 18 cycles per degree.

Referring to FIG. 1, a prior art contrast sensitivity chart 14 is illustrated. This chart includes contrast sensitivity rows for measuring human vision contrast sensitivity with 1.5 cycles per degree row A, 3.0 cycles per degree row B, 6.0 cycles per degree row C, 12.0 cycles per degree row D, and 18 cycles per degree row E.

Columns 1–9 are columns of decreasing contrast with column 1 having the highest contrast and column 9 having the lowest contrast. The patient undergoing vision contrast sensitivity testing is asked to identify tilt of the respective images. Such tilt is illustrated in right box 16, up box 18, and left box 20. This test is more fully described in Ginsburg U.S. Pat. No. 4,365,873 issued Dec. 28, 1982 entitled Spatial Frequency and Contrast Sensitivity Test Chart.

The results of the vision contrast sensitivity test will be an objectively determined outcome that is unique to the individual patient tested.

Figure 2:
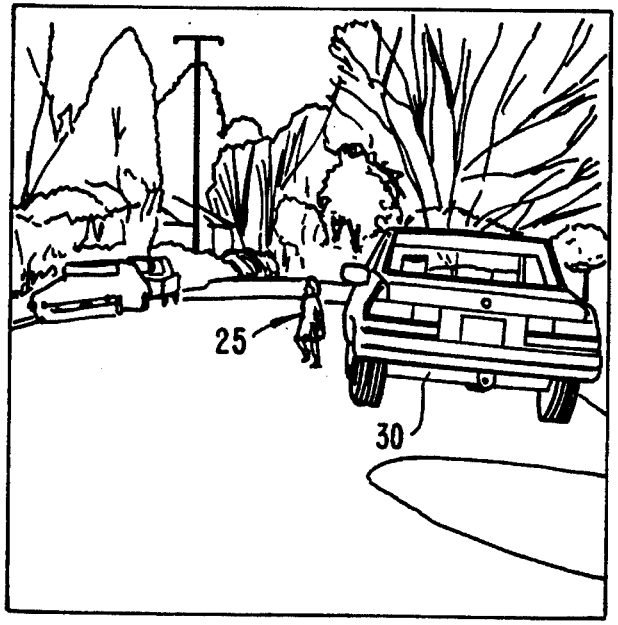
FIG. 2 is a view of a typical real world scene, this scene being the view from a driver's seat through the windshield of an automobile with a child shown running into the street between parked cars.

Referring to FIG. 2, a real world original image $I_R$ is illustrated. Real world image $I_R$ illustrates child 25 walking from in front of parked car 30. The view is typical of that taken through the windshield of a car being driven by a driver. Fortunately, in this case the driver is an emmetrope.

Figure 3:
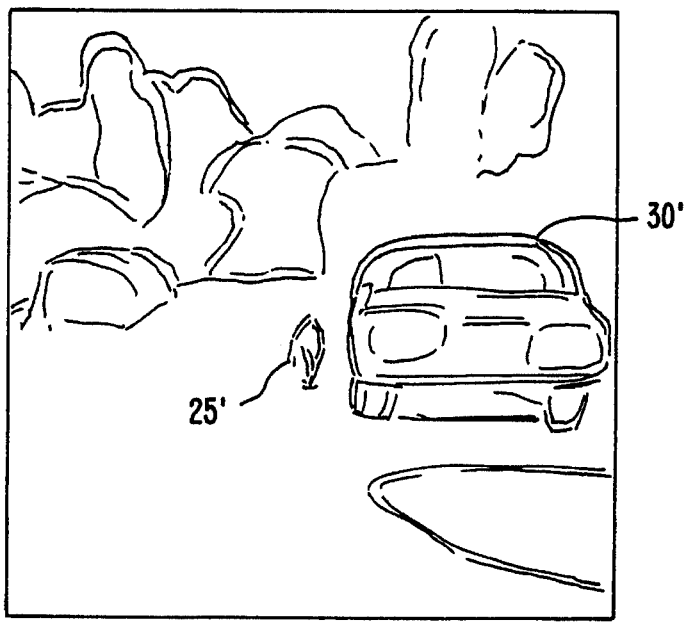
FIG. 3 is a view of an altered real world scene of the view of FIG. 2, illustrating an objectively measured degradation of the original real world images side by side with the view of FIG. 2.

Referring to FIG. 3, the view of a patient having impaired vision—say cataract impaired vision—is shown of the same scene. Parked car 30' is a blurred, low contrast mass while child 25' is barely visible. It will be observed that this latter picture is dramatic in at least two aspects.

First, an emmetrope viewing FIG. 3 immediately understands the peril of a patient with the observed vision driving. Second, even the patient with the impaired vision can understand the problem. Specifically, and observing FIG. 2 and 3 simultaneously, it will be understood that the patient will make the comparison through his degraded vision. The seriousness of the vision defect and possibly the need to undertake corrective surgery, for example the removal of the cataract obscured lens, is emphasized.

Having set forth the results of the test, attention may now be devoted to the process.

Figure 4:
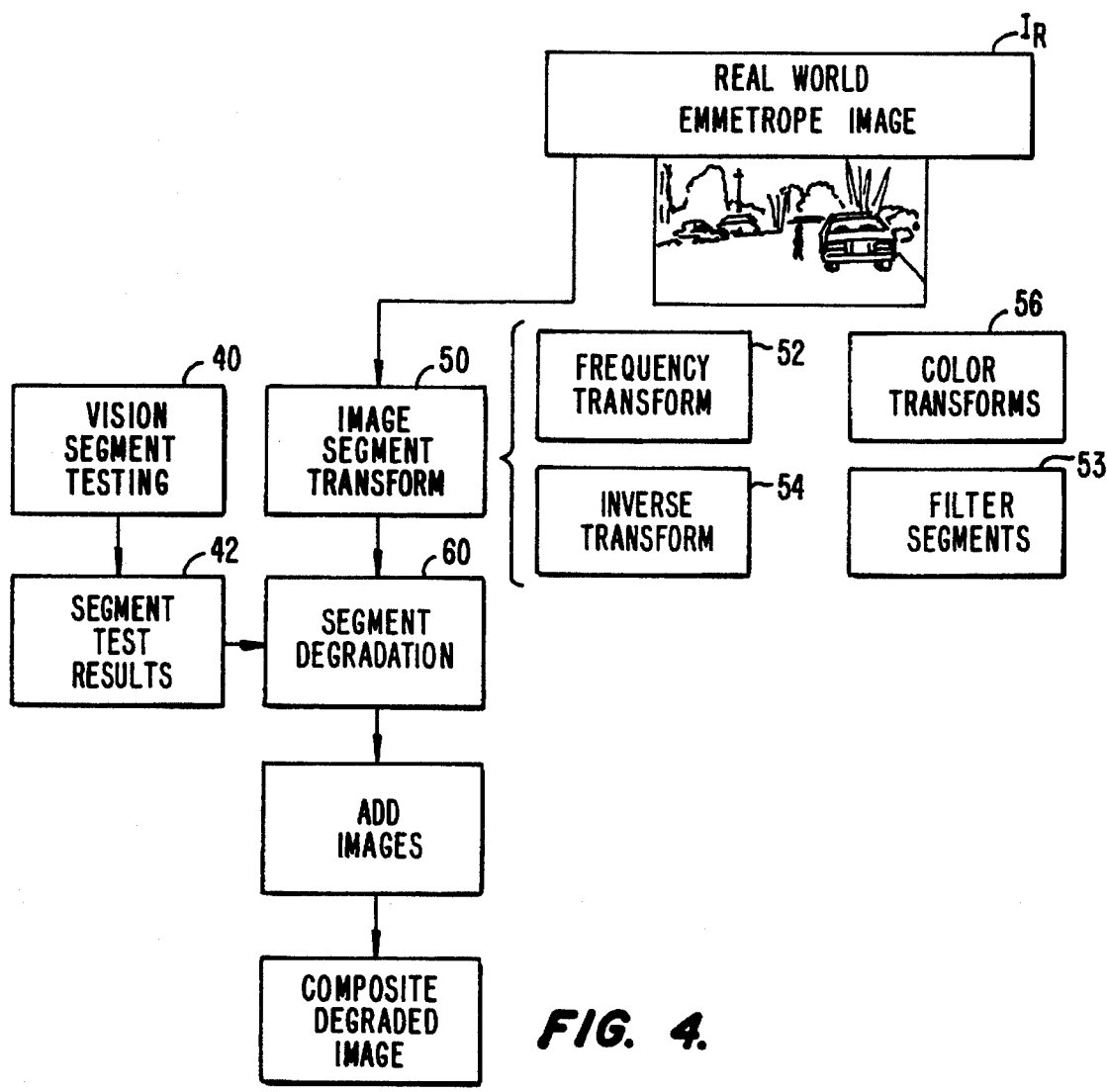
FIG. 4 is a flow diagram illustrating the general data processing required including objective measurement of the vision of the patient, corresponding segmentation of the real world emmetropic vision, degradation of the segmented images in accordance with the measured vision results and generation of the resultant composite view.

Referring to FIG. 4, the vision testing process can now be described. Specifically, vision segment testing 40 generates separate readings for separate segments tested. Such testing can result from contrast sensitivity chart 14 illustrated in FIG. 1. Test results are output to segment test results 42 and segment degradation 60.

Next, it is required that real world original image $I_R$ be processed. Specifically, such transformation occurs in image segment transform 50.

Referring further to FIG. 4, it can be seen that two types of image processing are there referenced. The first of these is frequency transform 52 followed by filter segments 53 and then frequency inverse transform 54. The second is color transforms 56. In this specification, the preferred technique of frequency transform 52, filter segments and frequency inverse transform 54 will be set forth first.

Figure 5:
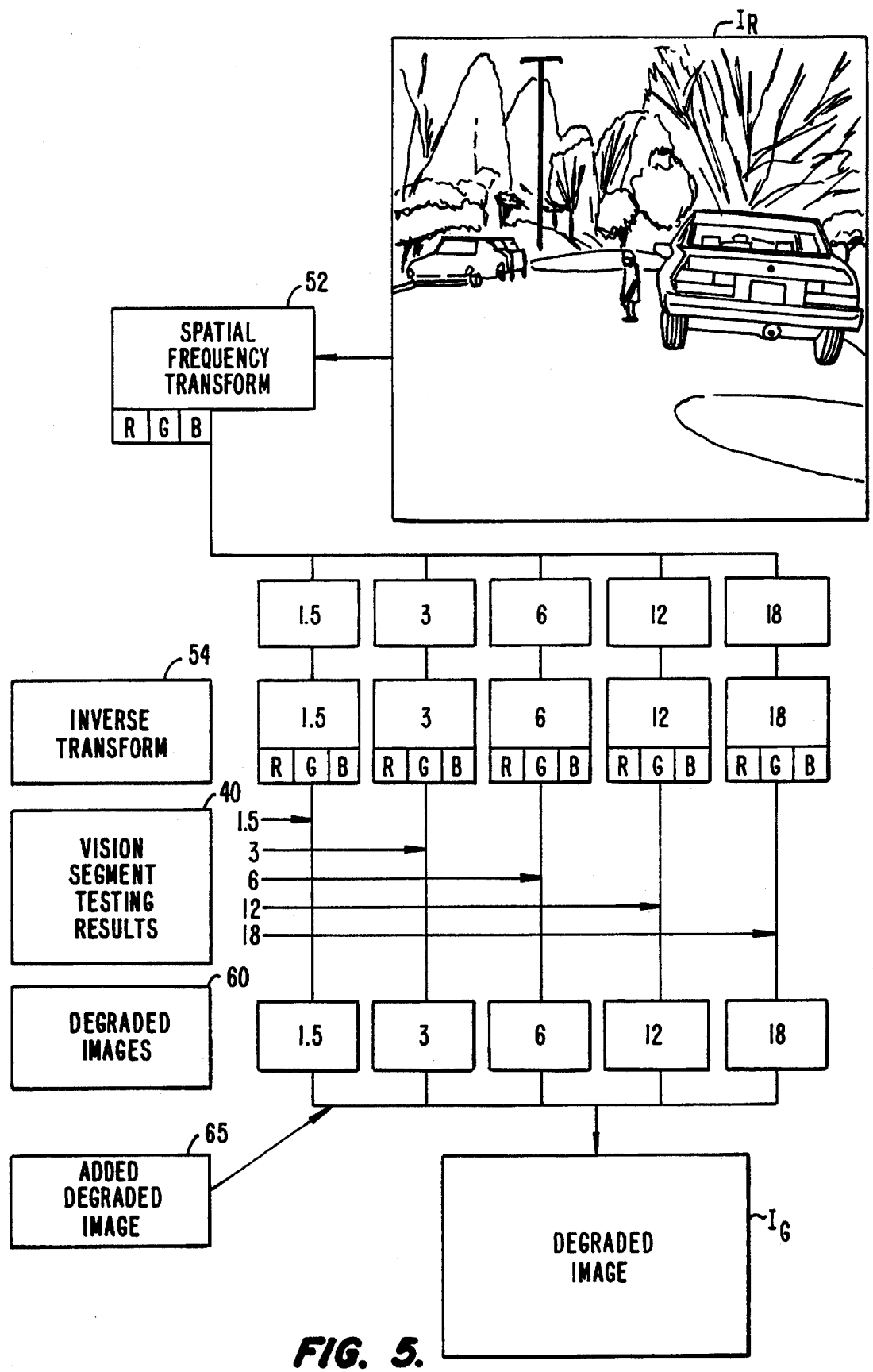
FIG. 5 is a flow diagram unique to vision contrast sensitivity testing illustrating vision testing in discrete two octave bands, fast Fourier transform of the original real world image from the spatial domain to the frequency domain, filtering the frequency domain into discrete octave bands, inverse transform from the frequency domain to the spatial domain, modifying the segmented images from vision testing results, and the linear addition of images degraded in measured amount in accordance with the testing protocol to produce the comparison image illustrated in FIG. 3.

The case of the contrast frequency transforms is set forth specifically with respect to FIG. 5. Simply stated, frequency transform 52 takes real world original image $I_R$ from the spatial domain and places the image in the frequency domain. This transform, however, is filtered into segments 53 unique to the particular frequency segment being utilized. Thus, there will be a first filtered transform for 1.5 cycles per degree row A, a second filtered transform for 3.0 cycles per degree row B, etc. Thereafter, inverse transform 54 on each filter segment will occur. Thus, and again, there will be a first inverse transform for 1.5 cycles per degree row A, a second inverse transform for 3.0 cycles per degree row B, etc.

Presuming that the person who took the test was an emmetrope, there would be no degradation of real world emmetropic image $I_R$. However, in the usual case, less than perfect vision will be encountered. Thus modification of real world original image $I_R$ on any image after the first transform can occur.

Referring to FIG. 4 and 5, this takes place in segment degradation step 60. Referring to FIG. 5, it will be understood that segment degradation step 60 is unique to each filter segment of the image. Assuming a less than perfect vision test in the 1.5 cycle per degree test, degradation or attenuation of the 1.5 cycle per degree image component will occur. Similarly, assuming a less than perfect vision test in the 3.0 cycle per degree test, degradation or attenuation of the 3.0 cycle per degree image component will occur. Corresponding image modification will occur for corresponding test segments and results.

This filtering occurs with the any process that is unique to a frequency or size such as filtering the transformation or convolution. In the case of a Fourier-like transform, degradation of an image segment can occur after the first transform and before the inverse transform, or more preferably after the inverse transform and before the image is added.

It will be understood that we prefer alteration of the images unique to a particular contrast sensitivity segment after frequency inverse transform 54. It turns out that taking any real world scene and performing first a Fourier transform from the spatial domain to the frequency domain, filtering into segments, and thereafter performing an inverse Fourier transform for that same spatial frequency segment from the frequency domain to the spatial domain is computationally intense. Computer time ranging to 3 hours for the transform and inverse transform is not unknown (depending upon picture size and density of information). This being the case, a computer program utilizing an inverse transform segment image is preferred.

Referring again to FIG. 5, it can be seen vision segment testing 40 produces on frequency inverse transform 54 for each of the test segments degradation of the images at segment degradation step 60. Thereafter, addition of degraded images 65 occurs. This results in patient specific degraded image $I_G$.

It goes without saying that the resultant patient specific degraded image $I_G$ is a most convenient medical record. It is a record that displays objectively the sum total of the patient's extant vision at the time of testing. Further, by comparison of patient specific degraded image $I_G$ with real world original image IR, a contrast of the patient's vision to that of an emmetrope can be made.

It will be understood that any vision test which divides and measures properties of human vision into discrete segments is suitable for use with this disclosed process. In the above explanation, it will be understood that a black and white image could be used. It is also possible and preferable to use this process with color.

For example, color images are especially suitable where the patient is tested for so-called "color blindness", that color blindness quantified, and a color image divided into its respective red, green, and blue segments and appropriate degraded in it respective red, green, and blue segments. This much is illustrated at the inverse transform with red R, green G and blue B.

Returning to FIG. 5, it can be seen that frequency inverse transform 54 now includes 18 separate images. Specifically, there is an inverse transform at each of the six frequency segments for each of the three colors; red R, green G, and blue U.

Figure 6:
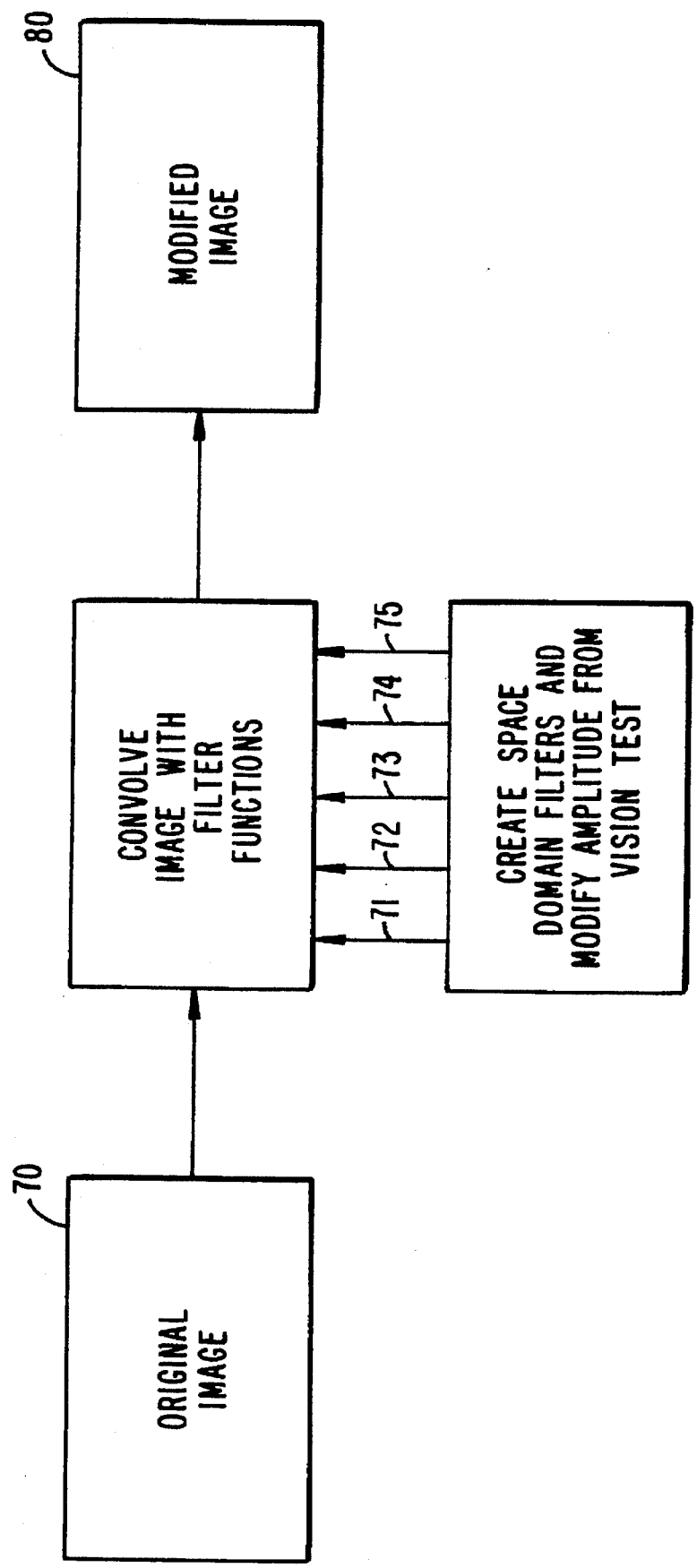
FIG. 6 is a block diagram illustrating one type of convolution processing where an image is modified by space domain filtering with amplitude modification determined by vision test results.

Referring to FIG. 6, the invention can be understood in terms of image convolution in the spatial domain. Specifically, image 70 is utilized. Pursuant to the disclosure herein, image 70 can be an original, color or a degraded image. Further, the disclosed procedure can be utilized to degrade or enhance the image.

Eye testing is not specifically illustrated. Eye testing can include frequency testing or testing for recognizable shapes utilizing, for example, convolution functions such as Gaussians. Such convolved images are known and techniques for applicable filter functions are set forth in at least *Visual Information Processing Based on Spatial Filters Constrained by Biological Data* by Arthur P. Ginsburg, Ph.D, AMRL-TR-78-129, Volume 1, December 1978.

Once eye testing occurs, eye test result can be utilized to modify filter function—preferably in bandwidth, shape, and amplitude. For each vision segment tested, a discrete filter function will be used for image modification. Here, we illustrate image modifications occurs with spatial convolutions 71–75 to image 70.

It will be understood that image convolution can occur with filter functions which correspond to measured size, shape or frequency sensitivity components of the eye.

Finally, each of the convolved images from spatial convolutions 71–75 is added to produce modified image 80. It will be understood that original image 70 may be enhanced instead of degraded by the illustrated process. For example, a pre-cataract image may be modified to illustrate postcataract surgery vision or.

It will be understood that when computer processing according to this invention is utilized, real time image processing is in effect possible. For example, utilizing the disclosed frequency testing, records can effectively be produced on a real time basis.

Other modification can occur as limited only by the scope of the appended claims. For example, instead of processing images, a look up table of recorded images may be utilized. Thereafter, the most closely corresponding image may be addressed in accordance with the teachings of this invention. Such addressing would utilize the vision test results to address that stored image which most closely corresponds to the particular control image modified in accordance with the vision test results. It is not required that the images be actively processed to practice this invention; locating images having close similarity to that called for by actual eye test results is sufficient.

What is claimed is:

1. In a process for measurement and recordation of actual image visibility by a subject compared to a preselected standard of image visibility by another subject having differing image visibility, the steps comprising:

selecting an image;

selecting a vision test having capability of detecting vision sensitivity in at least one segment of a preselected vision channel;

testing the vision sensitivity of the subject in the at least one segment of the preselected vision channel to generate test results for the at least one segment of the preselected vision channel;

filtering the image into at least one image segment corresponding to the at least one segment of the preselected vision channel;

changing the at least one image segment corresponding to the test results for the at least one segment of the preselected vision channel to produce a modified image segment;

replacing the at least one image segment with the modified image segment to produce a composite modified image including the modified image segment; and, displaying the composite modified image to emulate actual vision of the subject.

2. The process for the measurement and recordation of actual image visibility in accordance with claim 1 and wherein:

the step of selecting an image includes selecting an in focus, full contrast, color image.

3. The process for the measurement and recordation of actual image visibility in accordance with claim 1 and wherein:

the step of changing the at least one image segment includes degrading the at least one image segment.

4. The process for the measurement and recordation of actual image visibility in accordance with claim 1 and wherein:

the step of changing the at least one image segment includes enhancing the at least one image segment.

5. The process for the measurement and recordation of actual image visibility in accordance with claim 1 and wherein:

comparing the composite modified image to the selected image to provide an objective comparison of subject vision.

6. The process for the measurement and recordation of actual image visibility in accordance with claim 1 and wherein:

the step of selecting a vision test having capability of detecting vision sensitivity in at least one segment of a preselected vision channel includes selecting segments of vision contrast sensitivity; and, the step of filtering the image into at least one image segment corresponding to the at least one segment of the preselected vision channel includes filtering the image in corresponding selected segments of the vision contrast sensitivity.

7. The process for the measurement and recordation of actual image visibility in accordance with claim 6 and wherein:

the step of selecting a vision test having capability of detecting vision sensitivity in at least one segment of a preselected vision channel includes selecting two octave bands centered on 1.5, 3, 6, 12, and 18 cycles per degree; and, the step of filtering the image into at least one image segment corresponding to the at least one segment of the preselected vision channel includes filtering in selected two octave bands centered on 1.5, 3, 6, 12, 18 cycles per degree.

8. The process for the measurement and recordation of actual image visibility in accordance with claim 6 and wherein the step of filtering of the image includes:

generating a Fourier transform of the image for each selected frequency band; and, generating from the Fourier transform an inverse Fourier transform for each selected frequency band.

9. The process for the measurement and recordation of actual image visibility in accordance with claim 6 and wherein:

the step of selecting segments of vision contrast sensitivity includes testing the vision of the subject in red, green, and blue; and, the step of filtering the image includes filtering the image into red, green and blue segments.

10. The process for the measurement and recordation of actual image visibility in accordance with claim 1 and wherein:

the filtering the image step includes convolving an image; and, the replacing the image segment includes convolving the image segments with space domain filters corresponding to the selected vision segments.

11. In a process for the measurement and recordation of image visibility, the steps comprising:

selecting an image;

selecting a vision test having detected vision sensitivity in at least one segment of a preselected vision channel;

testing vision of the subject in the at least one segment of the preselected vision channel;

convolving the image into at least one modified image segment with filter functions corresponding to the tested vision of the subject in the at least one segment of the preselected vision channel; and, replacing the modified image segments to the selected image to produce a composite modified image.

12. In a process for the measurement and recordation of image visibility according to claim 11, the steps further comprising:

the testing of the vision of the subject includes spatial frequency testing.

13. In a process for the measurement and recordation of image visibility according to claim 11, the steps further comprising:

the convolving step includes convolving the image with filter functions having spatial frequency sensitivity.

* * * * *